(12) United States Patent
Amakawa et al.

(10) Patent No.: US 6,881,864 B2
(45) Date of Patent: Apr. 19, 2005

(54) PRODUCTION METHOD OF XYLYLENEDIAMINE

(75) Inventors: Kazuhiko Amakawa, Niigata (JP); Kazushi Gouroku, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/788,389

(22) Filed: Mar. 1, 2004

(65) Prior Publication Data

US 2005/0004399 A1 Jan. 6, 2005

(30) Foreign Application Priority Data

Mar. 7, 2003 (JP) .......................... 2003/061258

(51) Int. Cl.$^7$ ............................ C07C 209/48
(52) U.S. Cl. ........................................ 564/415
(58) Field of Search ........................... 564/415

(56) References Cited

U.S. PATENT DOCUMENTS

| | | | |
|---|---|---|---|
| 3,647,054 A | | 3/1972 | Tsubol et al. |
| 6,114,277 A | * | 9/2000 | Miura et al. ............... 502/301 |
| 6,476,267 B1 | * | 11/2002 | Fuchigami et al. ......... 564/385 |

FOREIGN PATENT DOCUMENTS

| | | |
|---|---|---|
| EP | 1 193 244 | 4/2002 |
| EP | 1 279 661 | 1/2003 |
| JP | 6-121929 | 5/1994 |

OTHER PUBLICATIONS

Communication and European Search Report mailed Jul. 26, 2004, for No. EP 04 00 4779.
M. Kawakatsu, et al., Xylylenediamine by hydrogenation of phthalonitrile, Chemical Abstracts No. XP002276589, and JP No. 38–008719 (Abstract only), Oct. 21, 1960.
K. Nakamura, et al., "Process for manufacturing high purity xylylenediamine", Chemical Abstracts No. XP002284399, and JP No. 2003–026638 (Abstract only), Jan. 29, 2003.
K. Amakawa, et al., "Process for manufacturing aromatic dimethylamine", Chemical Abstracts No. XP002276592, and JP No. 2003–327563 (Abstract only), Nov. 19, 2003.

* cited by examiner

Primary Examiner—Brian Davis
(74) Attorney, Agent, or Firm—Antonelli, Terry, Stout & Kraus, LLP

(57) ABSTRACT

In the method of the present invention, xylylenediamine is produced by a two-stage hydrogenation of a dicyanobenzene compound. In a first stage (a), the hydrogenation is performed until a conversion of nitrile groups reaches 90 mol % or higher and less than 99.9 mol %. In a second stage (b), the hydrogenation is further continued at temperatures 10° C. or more higher than in the step (a) until the conversion of nitrile groups reaches a level which is higher than that attained in the step (a) and equal to 99.5 mol % or more. In the present invention, a highly pure xylylenediamine containing a minimized amount of cyanobenzylamine is efficiently produced in a simple manner without needing a specific purification, and also without deteriorating the use efficiency of the catalyst while reducing the amount of the dicyanobenzene compound remaining not reacted and the generation of the intermediate cyanobenzylamine.

14 Claims, No Drawings

US 6,881,864 B2

PRODUCTION METHOD OF XYLYLENEDIAMINE

BACKGROUND OF THE INVENTION

1. Field of the Invention

The present invention relates to a production method of xylylenediamine by a continuous two-stage hydrogenation of a dicyanobenzene compound.

2. Description of the Prior Art

The production method of xylylenediamine by the hydrogenation of a corresponding dicyanobenzene compound in the presence of a catalyst is well known in the art. For example, Japanese Patent Publication No. 38-8719 discloses an autoclave batch-wise hydrogenation of a dicyanobenzene compound into the corresponding diamine in an alcohol in the presence of Raney nickel or Raney cobalt together with a trace amount of an caustic alkali. Japanese Patent Application Laid-Open No. 54-41804 discloses an autoclave batch-wise hydrogenation of a dicyanobenzene compound into the corresponding diamine in a mixed solvent of a lower alcohol and a cyclic hydrocarbon in the presence of a hydroxide or alkolate of alkali or alkaline earth metal together with a Raney nickel of Raney cobalt catalyst. Japanese Patent Application Laid-Open No. 6-121929 discloses an autoclave batch-wise hydrogenation of an isophthalonitrile compound into the corresponding diamine in a methanol-ammonia solvent in the presence of a Rh—Co-containing catalyst.

Japanese Patent Publication No. 53-20969 discloses a liquid-phase catalytic reduction of a dicyanobenzene compound by hydrogen in the presence of a Ni—Cu—Mo-containing catalyst. The catalytic reduction is performed by a fixed-bed continuous hydrogenation in the working examples. Japanese Patent Application Laid-Open No. 56-83451 discloses a production method of diamine in the presence of a slurry-bed Rh—Co-containing catalyst. "Process Handbook", Japan Petroleum Institute, 1978 discloses an industrial production process in which the starting nitrile is introduced into a hydrogenation reactor together with a solvent and a catalyst and hydrogenated therein under slurry conditions.

To yield xylylenediamine efficiently by hydrogenation, it is required to increase the progress of the hydrogenation of nitrile group into aminomethyl group (conversion of nitrile group) and minimize the amounts of non-reacted dicyanobenzene and intermediate cyanobenzylamine generated by the hydrogenation of only one of the nitrile groups. It is desirable that the concentration of cyanobenzylamine in the liquid mixture after hydrogenation is low, because the difference in the boiling points of cyanobenzylamine and the corresponding xylylenediamine is generally small to make the separation thereof by a usual distillation difficult. Therefore, it is preferred for the efficient production of xylylenediamine to proceed the hydrogenation into xylylenediamine efficiently and to minimize the concentration of cyanobenzylamine after the hydrogenation by increasing the conversion of nitrile groups, thereby making the purification of xylylenediamine easy.

One of the methods for increasing the conversion of nitrile groups is to prolong the contact time with a catalyst. To prolong the contact time, it is required for a fixed-bed reaction to use a large amount of catalyst in an increased size reactor while not changing the flow rate, and required for a batch-wise reaction to prolong the reaction time. These methods, however, are inexpedient for industrial production because of a poor use efficiency of catalyst, increased reactor costs, catalyst costs and a lowered productivity.

Another method for increasing the conversion of nitrile groups is to increase the reaction temperature. By increasing the reaction temperature, the amount of the dicyanobenzene compound remaining not reacted is reduced and the generation of cyanobenzylamine is prevented. However, high reaction temperatures sometimes increase unfavorable side reactions such as deamination and condensation to lower the yield of xylylenediamine.

As described above, in the known methods of hydrogenating the dicyanobenzene compound, it is difficult to sufficiently prevent the generation of cyanobenzylamine without deteriorating the use efficiency of catalyst and the yield of xylylenediamine. Thus, in the industrial hydrogenation of dicyanobenzene, it is practically impossible to completely prevent the generation of cyanobenzylamine. Therefore, to obtain a highly pure xylylenediamine with a low content of cyanobenzylamine, the conventional technique requires plural purification steps after the hydrogenation of the dicyanobenzene compound: a removal of cyanobenzylamine, which is difficult to separate by distillation, form xylylenediamine by a specific method such as an alkali treatment (Japanese Patent Publication No. 45-14777) and a treatment with iron-containing catalyst (Japanese Patent Application Laid-Open No. 57-27098); and a subsequent distillation.

Recently, a highly pure xylylenediamine with a low content of cyanobenzylamine is demanded particularly in the use thereof as the raw material of isocyanates. In such a use, the content of dicyanobenzene in xylylenediamine is required to be 0.02% by weight or less. Therefore, there has been a demand for developing an industrially advantageous method of producing a highly pure xylylenediamine with a low content of cyanobenzylamine.

As described above, in the production of xylylenediamine by the hydrogenation of the dicyanobenzene compound, it has been difficult to sufficiently prevent the generation of cyanobenzylamine without deteriorating the use efficiency of catalyst and the yield of xylylenediamine. Therefore, it has been required, particularly for the production of a highly pure xylylenediamine with a small content of cyanobenzylamine, to purify xylylenediamine by plural steps: a removal of cyanobenzylamine by a specific treatment and a subsequent distillation.

SUMMARY OF THE INVENTION

An object of the present invention is to solve the above problems and provide a method for producing xylylenediamine by the hydrogenation of a dicyanobenzene compound, which is capable of efficiently producing xylylenediamine while reducing the amounts of a non-reacted dicyanobenzene compound and an intermediate cyanobenzylamine, and which is capable of efficiently producing a highly pure xylylenediamine with a small content of cyanobenzylamine in a simple manner without needing a specific purification treatment.

As a result of extensive study on the production of xylylenediamine, the inventors have found that the above object can be attained by performing the hydrogenation in two steps under different conditions and regulating the conversion of nitrile groups in each step within a specific range. The present invention has been accomplished on the basis of this finding.

Thus, the present invention provides a method of producing xylylenediamine by hydrogenating a dicyanobenzene compound in the presence of a catalyst, which comprises a step (a) of performing the hydrogenation until a conversion of nitrile groups reaches 90 mol % or higher and less than 99.9 mol %, and a step (b) of further continuing the hydrogenation at temperatures 10° C. or more higher than a reaction temperature of the step (a) until the conversion of nitrile groups reaches a level which is higher than that attained in the step (a) and equal to 99.5 mol % or more.

According to the present invention, xylylenediamine is produced by the hydrogenation of a dicyanobenzene compound in high yields while reducing the amounts of the dicyanobenzene compound remaining not reacted and the generation of the intermediate cyanobenzylamine. In addition, a highly pure xylylenediamine with a minimized amount of cyanobenzylamine is efficiently produced by a simple method which requires no specific purification treatment. Thus, the present invention is of industrially significant values.

DETAILED DESCRIPTION OF THE INVENTION

The present invention will be described below in more detail.

The dicyanobenzene compound referred to in the present invention means a compound having a benzene ring substituted by two nitrile groups, and exemplified by isophthalonitrile and terephthalonitrile. The dicyanobenzene compound may also include compounds having the benzene ring substituted, in addition to two nitrile groups, by a halogen atom such as fluorine and chlorine, an alkyl group such as methyl group and ethyl group and an alkoxy group such as methoxy group and ethoxy group, as exemplified by 2-chloroterephthalonitrile, 5-methylisophthanonitrile and 4-methylisophthanonitrile. These compounds are converted into the corresponding xylylenediamines by the hydrogenation of the invention. Of the above, isophthalonitrile and terephthalonitrile are particularly suitable for the process of the invention. Two or more of the above dicyanobenzene compounds may be hydrogenated simultaneously.

In the present invention, the hydrogenation of the steps (a) and (b) is performed in liquid phase preferably using a reaction solvent. As the reaction solution, various solvents which are stable under the hydrogenation conditions may be used, for example, hydrocarbon solvents such as toluene, xylene and trimethylbenzene; ether solvents such as tetrahydrofuran and dioxane; lower aliphatic amide solvents such as dimethylformamide and dimethylacetamide; alcohol solvents such as methanol, ethanol and propanol; and ammonia. These solvents may be used in combination of two or more. Since the use of ammonia increases the yield of xylylenediamine, it is preferred to use ammonia as a part of the solvent. The amount of the solvent to be used in each of the steps (a) and (b) is preferably 1 to 99 parts by weight, more preferably 2 to 99 parts by weight, and still more preferably 5 to 99 parts by weight per one part by weight of the dicyanobenzene compound initially charged in the step (a).

Hydrogen to be used for hydrogenating the dicyanobenzene compound may include impurities inert to the hydrogenation such as methane and nitrogen. However, a high impurity concentration is industrially disadvantageous because a higher total reaction pressure is required to attain a necessary hydrogen partial pressure. Therefore, the hydrogen concentration in the hydrogenation gas is preferably 50 mol % or more. The hydrogen pressure in the hydrogenation is preferably 0.5 to 30 MPa, more preferably 1 to 20 MPa at hydrogenation temperatures for both the steps (a) and (b).

The catalyst for the hydrogenation to be used in the steps (a) and (b) may be a known supported or non-supported metal catalyst, Raney catalyst, etc. Preferred is a catalyst containing at least one metal as the active metal component such as nickel, cobalt, palladium, ruthenium and rhodium, with a catalyst containing nickel and/or cobalt being more preferred and a nickel-containing catalyst being still more preferred. The support for the supported catalyst may include alumina, silica, titania and zirconia. The catalyst may be cocatalyzed, if necessary, by at least one component selected from the group consisting of Li, Na, K, Rb, Cs, Be, Ca, Ba, Ti, Cu, Cr, Zn, Mn, Mg, Fe, Ga, Ge, Nb, Ir, Pt, Bi, Al, Si, In, Sr, Ce and Mo.

Although depending on the kinds of catalyst and reaction conditions, the amount of the catalyst to be used in each of the steps (a) and (b) of the slurry-bed hydrogenation is preferably 0.1 to 200 parts by weight, more preferably 0.2 to 100 parts by weight per 100 parts by weight of the initially charged dicyanobenzene compound. In the fixed-bed hydrogenation, the amount of the catalyst to be used in the step(a) is preferably 0.1 to 10000 parts by weight, more preferably 0.2 to 5000 parts by weight per one part by weight of the hourly fed dicyanobenzene compound, and preferably 0.1 to 5000 parts by weight, more preferably 0.2 to 2000 parts by weight in the step (b) per one part by weight of the dicyanobenzene compound which is hourly fed in the step (a).

In the present invention, the hydrogenation system may be added with an additive, for example, a hydroxide or alkolate of an alkali metal or alkaline earth metal such as lithium hydroxide, sodium hydroxide and potassium hydroxide to promote the hydrogenation and increase the yield of xylylenediamine.

The process of the present invention includes two steps: a step (a) of performing the hydrogenation until the conversion of nitrile groups (nitrile conversion) reaches 90 mol % or higher and less than 99.9 mol %, and a step (b) of further continuing the hydrogenation at temperatures 10° C. or more higher than the reaction temperature of the step (a) until the conversion of nitrile groups (nitrile conversion) reaches a level which is higher than that attained in the step (a) and equal to 99.5 mol % or more. The conversion of nitrile groups (nitrile conversion) referred to herein is the proportion of the total number of reacted nitrile groups to the total number of nitrile groups in the starting dicyanobenzene compound, and defined by the following formula 1:

$$\text{Nitrile Conversion (\%)} = ((A \times 2) - (B \times 2) - C)/(A \times 2) \times 100 \qquad (1)$$

wherein A is the molar number of the supplied dicyanobenzene compound, B is the molar number of the dicyanobenzene compound remaining not reacted and C is the molar number of the generated cyanobenzylamine.

In the step (a), the hydrogenation is performed until the nitrile conversion reaches 90 mol % or higher and less than 99.9 mol %, preferably 90 to 99.5 mol %. Although depending on the kinds of catalyst, reaction solvent and starting dicyanobenzene compound, the reaction temperature of the step (a) is suitably selected so as to prevent the undesired side reactions due to high temperatures. The reaction temperature of the step (a) is preferably 20 to 200° C., more preferably 20 to 180° C., and still more preferably 30 to 160° C.

In the step (b), the hydrogenation is performed at temperatures 10° C. or more higher than the reaction temperature of the step (a) until the nitrile conversion becomes higher than that attained in the step (a). The nitrile conversion to be finally attained in the step (b) is 99.5 mol % or more, preferably 99.9 mol % or more, and still more preferably 99.99 mol % or more. The nitrile conversion in the step (b) may reach as high as about 99.9995 mol % at highest. When the reaction temperature of the step (a) varies within the above range, the reaction temperature of the step (b) is set to temperatures 10° C. or more higher than the mean of the maximum and minimum temperatures until the nitrile conversion reaches 90 mol %. Although depending on the kinds of catalyst, reaction solvent and starting dicyanobenzene compound, the reaction temperature of the step (b) is preferably 80 to 250° C., more preferably 80 to 200, and still more preferably 80 to 180° C.

By performing the hydrogenation until the nitrile conversion reaches 90 mol % or higher and less than 99.9 mol % in the step (a), and then further performing the hydrogenation at higher temperatures in the step (b), it becomes possible to prevent undesired side reactions due to high reaction temperatures from occurring in the step (a) and to sufficiently increase the nitrile conversion in the step (b), thereby reducing the amount of dicyanobenzene compound remaining not reacted and the generation of intermediate cyanobenzylamine. As a result of researches made by the inventors, it has been surprisingly found that undesired side reactions due to high reaction temperatures hardly occur in the step (b) irrespective of higher reaction temperatures than used in the step (a), and further found that both a high yield of xylylenediamine and a sufficiently high nitrile conversion are simultaneously attained by the two-stage hydrogenation of the steps (a) and (b).

In the hydrogenation performed only by the step (a) without employing the step (b), a prolonged contact time is needed to achieve an intended nitrile conversion if the reaction temperature is low, thereby reducing the efficiency. If the reaction temperature is high, side reactions become significant to reduce the yield of xylylenediamine.

The hydrogenation may be performed in either of fixed bed method or slurry bed method, or in either of batch-wise manner or continuous manner, with a fixed-bed continuous flow method being preferred because it is easy and simple. Practically, the steps (a) and (b) are performed, for example, in the following manners (1) to (3):

(1) a slurry-bed batch-wise manner where the hydrogenation is performed until the nitrile conversion reaches 90 mol % or more and less than 99.9 mol % (step (a)), and thereafter the reaction mixture is heated in the same reactor to a temperature 10° C. or more higher than in the step (a) to further perform the hydrogenation until the nitrile conversion reaches 99.5 mol % or more (step (b));

(2) a slurry-bed or fixed-bed continuous flow manner where the hydrogenation is performed in a first reactor until the nitrile conversion reaches 90 mol % or more and less than 99.9 mol % (step (a)), and thereafter the reaction mixture is introduced into a second reactor and heated to a temperature 10° C. or more higher than in the first reactor to further perform the hydrogenation until the nitrile conversion reaches 99.5 mol % or more (step (b)); and (3) a fixed-bed continuous flow manner where the hydrogenation is performed in a temperature gradient reactor having a first region for performing the hydrogenation until the nitrile conversion reaches 90 mol % or more and less than 99.9 mol % (step (a)), and a second region for further continuing the hydrogenation at temperatures 10° C. or more higher than in the first region until the nitrile conversion reaches 99.5 mol % or more (step (b)).

The temperature difference between the steps (a) and (b) can be easily developed by disposing a known heat exchanger between the steps (a) and (b) or to the step (b). Alternatively, the heat evolved in the hydrogenation of dicyanobenzene compound may be utilized to develop the temperature difference between the steps (a) and (b). Namely, the heat is evolved in the step (a) for performing the hydrogenation until the nitrile conversion reaches 90 mol % or more. The evolved heat, if not removed, raises the temperature of the reaction mixture from the step (a) to develop the temperature difference between the steps (a) and (b), thereby making the process advantageous in view of energy consumption and costs of heat exchanger. The amount of the evolved hydrogenation heat can be calculated from the amount of the reaction liquid, the amount of nitrile group in unit amount of reaction solution and the hydrogenation heat per unit amount of nitrile group.

In the present invention, xylylenediamine is produced in high yields while reducing the amount of dicyanobenzene compound remaining not reacted and the generation of intermediate cyanobenzylamine. Therefore, the molar ratio of cyanobenzylamine to xylylenediamine at the outlet of reactor can be reduced to preferably 0.01 or less, more preferably 0.002 or less, still more preferably 0.0002 or less, and can be minimized to 0.00001 (typical detection limit of gas-chromatography) by suitably selecting the production conditions. To lower the molar ratio of cyanobenzylamine to xylylenediamine at the outlet of reactor, it is important to choose proper reaction conditions in the step(b). The molar ratio of cyanobenzylamine to xylylenediamine at the outlet of reactor can be lowered by adjusting reaction temperature and contact time with a catalyst in the step(b). In the known hydrogenation of the dicyanobenzene compound, it has been difficult to sufficiently prevent the generation of the cyanobenzylamine without reducing the use efficiency of catalyst and the yield of xylylenediamine. In particular, it has been practically impossible to reduce the molar ratio of cyanobenzylamine to xylylenediamine into a level as extremely low as 0.0002 or less. The invention has made it possible to reduce the molar ratio of cyanobenzylamine to xylylenediamine into an extremely low level without sacrificing the use efficiency of catalyst and the yield of xylylenediamine.

After removing the gaseous components from the reaction mixture taken out of the outlet of reactor, xylylenediamine is separated from the residual liquid components by a suitable purification method. The purification of xylylenediamine can be performed relatively easier if the molar ratio of cyanobenzylamine to xylylenediamine at the reactor outlet is 0.01 or less. The purification method may be selected according to the desired quality of xylylenediamine, and the purification by distillation is generally suitable. As noted above, the separation of cyanobenzylamine from xylylenediamine is difficult by distillation. Therefore, to obtain a highly pure xylylenediamine with a minimized content of cyanobenzylamine, it is necessary to make the molar ratio of cyanobenzylamine to xylylenediamine at the reactor outlet as low as possible according to the desired quality (maximum allowable content of cyanobenzylamine). Since a molar ratio of cyanobenzylamine to xylylenediamine as low as 0.0002 or less can be attained at the reactor outlet in the present invention, a highly pure xylylenediamine with a cyanobenzylamine content of 0.02% by weight or less, preferably 0.001 to 0.01% by weight can be obtained by a simple purification process, for example, by only distillation. Such a highly pure xylylenediamine is suitably used in various uses, such as raw materials for isocyanates, in which only a small amount of remaining cyanobenzylamine should be avoided.

To remove cyanobenzylamine, the specific treatment such as an alkali treatment (Japanese Patent Publication No. 45-14777) and a treatment with iron-containing catalyst (Japanese Patent Application Laid-Open No. 57-27098) as mentioned above may be combinedly used in the present invention.

The present invention will be explained in more detail by reference to the following example which should not be construed to limit the scope of the present invention.

EXAMPLE 1

Preparation of Catalyst

Into 1 kg of pure water, were dissolved 305.0 g of nickel nitrate hexahydrate $(Ni(NO_3)_2.6H_2O)$, 6.5 g of copper nitrate trihydrate $(Cu(NO_3)_2.3H_2O)$ and 7.1 g of chromium nitrate nonahydrate $(Cr(NO_3)_3.9H_2O)$ at 40° C. To the resultant aqueous solution, 29.6 g of diatomaceous earth was dispersed at 40° C. under stirring, and then an aqueous solution prepared by dissolving 128.6 g of sodium carbonate $(Na_2CO)$ in 1 kg of pure water at 40° C. was added under vigorous stirring, thereby preparing a precipitation slurry. The precipitation slurry was heated to 80° C., kept at there for 30 min and filtered. The collected precipitation was washed, dried at 110° C. for 15 h, and calcined at 380° C. for 18 h in air. After blended with 3% by weight of graphite, the calcined powder was made into 3.0 mm$\phi$×2.5 mm tablets. The tablets were reduced at 400° C. in hydrogen gas stream, and then, stabilized by oxidizing treatment at room temperature to 40° C. for 15 h in a stream of dilute oxygen gas (oxygen/nitrogen=1/99 by volume). Thereafter, the tablets were crushed and classified into a particle size of 12 to 28 mesh to obtain a crushed catalyst (Catalyst A).

Hydrogenation

Two reaction tubes of 10 mm inner diameter were connected lengthwise to form a vertical fixed-bed reactor having an upper reaction tube for the step (a) and a lower reaction tube for the step (b). The upper and lower reaction tubes were equipped with respective heaters so as to independently control the reaction temperatures. After packing 5 g of Catalyst A in a packing height of 65 mm in each of the upper and lower reaction tubes, the packed catalysts were reduced and activated at 200° C. under hydrogen gas flow. The hydrogenation was performed under a reaction pressure of 12 MPa at a reaction temperature of 70° C. in the upper reaction tube and 110° C. in the lower reaction tube, while supplying a liquid raw material of isophthalonitrile (IPN), m-xylylene (MX) and ammonia $(NH_3)$ in a proportion of IPN:MX:$NH_3$=10:10:80 by weight and hydrogen gas from the top of the reactor. The liquid raw material and hydrogen gas were supplied at a rate of 60 g/h and 20 NL/h (N: normal condition) so that a nitrile conversion of 90 mol % or more and less than 99.9 mol % was attained at the outlet of the upper reaction tube, and a nitrile conversion of 99.5 mol % or more and higher than that attained at the outlet of the upper reaction tube was attained at the outlet of the lower reaction tube. The reaction liquids sampled from the outlets of the upper and lower reaction tubes were analyzed by gas chromatography. At the outlet of the upper reaction tube, the nitrile conversion was 91.6 mol %, the residue of isophthalonitrile was 0.3 mol %, the yield of m-xylylenediamine was 76.0 mol %, and the yield of 3-cyanobenzylamine was 16.3 mol %. At the outlet of the lower reaction tube, the nitrile conversion was 99.995 mol %, the residue of isophthalonitrile was 0.0 mol %, the yield of m-xylylenediamine was 91.3 mol %, and the yield of 3-cyanobenzylamine was 0.01 mol %.

Purification of Xylylenediamine

After removing gaseous components from the reaction mixture taken out of the outlet of the reactor, ammonia was removed by gradual evacuation to obtain a crude xylylenediamine liquid, which was then subject to batch distillation in a glass flask under reduced pressure. After removing m-xylylene at 10 kPa, the distillation was continued at 1 kPa to obtain m-xylylenediamine as the major distillate. The purity of m-xylylenediamine thus obtained was 99.9% by weight or more and the concentration of 3-cyanobenzylamine was 0.01% by weight or less.

EXAMPLE 2

The hydrogenation was performed in the same manner as in Example 1 except for setting the reaction temperatures in the upper and lower reaction tubes to 80° C. and 110° C. The reaction liquids sampled from the outlets of the upper and lower reaction tubes were analyzed by gas chromatography. At the outlet of the upper reaction tube, the nitrile conversion was 99.55 mol %, the residue of isophthalonitrile was 0.0 mol %, the yield of m-xylylenediamine was 91.5 mol %, and the yield of 3-cyanobenzylamine was 0.9 mol %. At the outlet of the lower reaction tube, the nitrile conversion was 99.99 mol % or more, the residue of isophthalonitrile was 0.0 mol %, the yield of m-xylylenediamine was 92.4 mol %, and the yield of 3-cyanobenzylamine was 0.004 mol %.

COMPARATIVE EXAMPLE 1

Hydrogenation

The hydrogenation was performed in the same manner as in Example 1 except for setting both the reaction temperatures in the upper and lower reaction tubes to 70° C. The reaction liquids sampled from the outlets of the upper and lower reaction tubes were analyzed by gas chromatography. At the outlet of the upper reaction tube, the nitrile conversion was 90.5 mol %, the residue of isophthalonitrile was 0.3 mol %, the yield of m-xylylenediamine was 73.2 mol %, and the yield of 3-cyanobenzylamine was 18.4 mol %. At the outlet of the lower reaction tube, the nitrile conversion was only 99.4 mol %. As a result, the residue of isophthalonitrile was 0.0 mol %, the yield of m-xylylenediamine was 89.9 mol %, and the yield of 3-cyanobenzylamine was 1.3 mol %.

Purification of Xylylenediamine

Gaseous components and ammonia were removed in the same manner as in Example 1 from the reaction mixture taken out of the outlet of the reactor to obtain a crude xylylenediamine liquid, which was then distilled. However, the resultant xylylenediamine contained 1% by weight or more of cyanobenzylamine. Separately, after adding sodium hydroxide and water, the crude xylylenediamine liquid was heat-treated at 180° C. for 3 h, and then distilled. The content of cyanobenzylamine in the resultant xylylenediamine was 0.01% by weight or less. Thus, to produce xylylenediamine with a small content of cyanobenzylamine, the hydrogenation which failed to meet the conditions of the present invention required an additional purification step in addition to distillation.

COMPARATIVE EXAMPLE 2

The hydrogenation was performed in the same manner as in Example 1 except for setting both the reaction temperatures in the upper and lower reaction tubes to 110° C. The reaction liquids sampled from the outlets of the upper and lower reaction tubes were analyzed by gas chromatography. At the outlet of the upper reaction tube, the nitrile conversion reached 99.9 mol %. The residue of isophthalonitrile was 0.0 mol %, the yield of m-xylylenediamine was 89.7 mol % and the yield of 3-cyanobenzylamine was 0.01 mol %. At the outlet of the lower reaction tube, the nitrile conversion was 99.995 mol %, the residue of isophthalonitrile was 0.0 mol %, the yield of m-xylylenediamine was 89.2 mol %, and the yield of 3-cyanobenzylamine was 0.00 mol %. Since the nitrile conversion reached 99.9 mol % at the outlet of the upper reaction tube, the yield of xylylenediamine was reduced.

EXAMPLE 3

Hydrogenation

Into a 1-L autoclave equipped with an electromagnetic stirrer, 4 g of Raney nickel catalyst ("NDHT" manufactured by Kawaken Fine Chemicals Co., Ltd.) was charged. Then, 60 g of terephthalonitrile, 60 g of MX and 120 g of methanol were charged into the autoclave and the inner atmosphere thereof was replaced with nitrogen. After introducing 120 g of $NH_3$, the autoclave was heated to 80° C. Then, hydrogen gas was introduced into the autoclave to perform the hydrogenation under 8 MPaG at 80° C. After initiating the hydrogenation, the reaction liquids were sampled at regular time intervals and analyzed by gas chromatography. After three hours from the initiation, the nitrile conversion reached 97.9 mol %. At this time, the residue of terephthalonitrile was 0.0 mol %, the yield of p-xylylenediamine was 79.0 mol %, and the yield of 4-cyanobenzylamine was 4.3 mol %. After three hours from the initiation, the reaction temperature was raised to 120° C. to continue the hydrogenation for 1.5 h (overall reaction time=4.5 h). The results of gas chromatographic analysis showed that the nitrile conversion was 99.99 mol %, the residue of terephthalonitrile was 0.0 mol %, the yield of p-xylylenediamine was 83.9 mol %, and the yield of 4-cyanobenzylamine was 0.015 mol %.

Purification of Xylylenediamine

After releasing the pressure, MX and methanol were removed from the recovered reaction liquid in a rotary evaporator. By distilling the resultant solution under 0.5 kPa, p-xylylenediamine was obtained as the major distillate. The purity was 99.9% by weight or more and the content of 4-cyanobenzylamine was 0.016% by weight.

COMPARATIVE EXAMPLE 3

Hydrogenation

The procedure of Example 3 was repeated except for performing the hydrogenation for 6 h at a constant reaction temperature of 80° C. After 6 h of the initiation of hydrogenation, the reaction liquid was analyzed by gas chromatography. The residue of terephthalonitrile was 0.0 mol %, the yield of p-xylylenediamine was 82.2 mol %, and the yield of 4-cyanobenzylamine was 0.4 mol %. Although the hydrogenation was continued longer than in Example 3, a larger amount of the intermediate 4-cyanobenzylamine remained.

Purification of Xylylenediamine

After releasing the pressure, MX and methanol were removed from the recovered reaction liquid in a rotary evaporator. By distilling the resultant solution under 0.5 kPa, p-xylylenediamine was obtained as the major distillate. The obtained p-xylylenediamine contained 0.4% by weight of 4-cyanobenzylamine.

COMPARATIVE EXAMPLE 4

The procedure of Example 3 was repeated except for performing the hydrogenation for 4.5 h at a constant reaction temperature of 120° C. The results of gas chromatographic analysis showed that the residue of terephthalonitrile was 0.0 mol %, the yield of p-xylylenediamine was 74.2 mol %, and the yield of 4-cyanobenzylamine was 0.01 mol %.

EXAMPLE 4

Into a 1-L autoclave equipped with an electromagnetic stirrer, 8 g of a 380° C. hydrogen-reduced cobalt catalyst supported on diatomaceous earth ("G-67" manufactured by Nissan Girdler Catalyst Co., Ltd.; cobalt content=56% by weight) was charged. Then, 60 g of IPN, 60 g of MX and 120 g of methanol were charged into the autoclave and the inner atmosphere thereof was replaced with nitrogen. After introducing 120 g of $NH_3$, the autoclave was heated to 95° C. Then, hydrogen gas was introduced into the autoclave to perform the hydrogenation under 12 MPaG at 95° C. After initiating the hydrogenation, the reaction liquids were sampled at regular time intervals and analyzed by gas chromatography. After three hours from the initiation, the nitrile conversion reached 95.6 mol %. At this time, the residue of isophthalonitrile was 0.0 mol %, the yield of m-xylylenediamine was 77.5 mol %, and the yield of 3-cyanobenzylamine was 8.9 mol %. After three hours from the initiation, the reaction temperature was raised to 130° C. to continue the hydrogenation for 1.5 h (overall reaction time=4.5 h). The results of gas chromatographic analysis showed that the nitrile conversion was 99.99 mol %, the residue of isophthalonitrile was 0.0 mol %, the yield of m-xylylenediamine was 86.7 mol %, and the yield of 3-cyanobenzylamine was 0.01 mol %.

COMPARATIVE EXAMPLE 5

The procedure of Example 4 was repeated except for performing the hydrogenation for 6 h at a constant reaction temperature of 95° C. After 6 h of the initiation of hydrogenation, the reaction liquid was analyzed by gas chromatography. The residue of isophthalonitrile was 0.0 mol %, the yield of m-xylylenediamine was 84.4 mol %, and the yield of 3-cyanobenzylamine was 1.1 mol %. Although the hydrogenation was continued longer than in Example 4, a larger amount of the intermediate 3-cyanobenzylamine remained.

COMPARATIVE EXAMPLE 6

The procedure of Example 4 was repeated except for performing the hydrogenation for 4.5 h at a constant reaction temperature of 130° C. The results of gas chromatographic analysis showed that the residue of isophthalonitrile was 0.0 mol %, the yield of m-xylylenediamine was 81.2 mol %, and the yield of 3-cyanobenzylamine was 0.01 mol %.

Xylylenediamines produced by the present invention are useful compounds which are used in wide industrial fields as the materials for the production of resin hardeners, nylon, polyurethane, rubber chemicals, paper processing agents, fiber finishing agents, etc. According to the present invention, highly pure xylylenediamines are efficiently produced in simple manner. Therefore, the production method of the present invention is of great industrial value.

What is claimed is:

1. A method of producing xylylenediamine by hydrogenating a dicyanobenzene compound in the presence of a catalyst, which comprises a step (a) of performing the hydrogenation until a conversion of nitrile groups reaches 90 mol % or higher and less than 99.9 mol %, and a step (b) of further continuing the hydrogenation at temperatures 10° C. or more higher than a reaction temperature of the step (a) until the conversion of nitrile groups reaches a level which is higher than that attained in the step (a) and equal to 99.5 mol % or more.

2. The method according to claim 1, wherein the conversion of nitrile groups at an outlet of a reactor is 99.9 mol % or more.

3. The method according to claim 1, wherein the conversion of nitrile groups at an outlet of a reactor is 99.99 mol % or more.

4. The method according to claim 1, wherein a molar ratio of cyanobenzylamine to xylylenediamine is 0.01 or less at an outlet of a reactor.

5. The method according to claim 1, wherein a molar ratio of cyanobenzylamine to xylylenediamine is 0.002 or less at an outlet of a reactor.

6. The method according to claim 1, wherein a molar ratio of cyanobenzylamine to xylylenediamine is 0.0002 or less at an outlet of a reactor.

7. The method according to claim 1, further comprising a step of purifying xylylenediamine from the step (b) to produce a purified xylylenediamine having a content of cyanobenzylamine of 0.02% by weight or less.

8. The method according to claim 1, wherein a reaction temperature of the step (b) is 80 to 250° C.

9. The method according to claim 1, wherein the hydrogenation of each of the step (a) and the step (b) is performed in a fixed bed reactor.

10. The method according to claim 1, wherein the temperature of the step (b) is maintained 10° C. or more higher than the reaction temperature of the step (a) by heat evolved in the step (a).

11. The method according to claim 1, wherein the catalyst is a nickel and/or cobalt-containing catalyst.

12. The method according to claim 1, wherein the catalyst is a nickel-containing catalyst.

13. The method according to claim 1, wherein the dicyanobenzene compound is isophthalonitrile and/or terephthalonitrile.

14. The method according to claim 1, wherein the hydrogenation of each of the step (a) and the step (b) is performed in a solvent containing ammonia.

* * * * *